(12) United States Patent
Attolino et al.

(10) Patent No.: US 8,198,459 B2
(45) Date of Patent: Jun. 12, 2012

(54) METHOD FOR THE PREPARATION OF RUFINAMIDE

(75) Inventors: Emanuele Attolino, Palagiano (IT); Lino Colombo, Pavia (IT); Ilaria Mormino, Milan (IT); Pietro Allegrini, San Donato Milanese (IT)

(73) Assignee: Dipharma Francis S.r.l., Baranzate (MI) (IT)

( * ) Notice: Subject to any disclaimer, the term of this patent is extended or adjusted under 35 U.S.C. 154(b) by 19 days.

(21) Appl. No.: 12/722,693

(22) Filed: Mar. 12, 2010

(65) Prior Publication Data

US 2010/0234616 A1 Sep. 16, 2010

(30) Foreign Application Priority Data

Mar. 16, 2009 (IT) ............................... MI2009A0394
Mar. 23, 2009 (IT) ............................... MI2009A0444

(51) Int. Cl.
C07D 249/00 (2006.01)
(52) U.S. Cl. ........................................ 548/255; 548/362
(58) Field of Classification Search .................. 548/255, 548/362

See application file for complete search history.

(56) References Cited

U.S. PATENT DOCUMENTS 4,789,680 A * 12/1988 Meier ............................ 514/359

OTHER PUBLICATIONS

Orlinkska, et al., Applied Catalysis A: General, 287, 2005, pp. 68-74.*

Ebner et al., "Synthesis of novel oxazolidinone antimicrobial agents", Bioorganic & Medicinal Chemistry, 16 (2008), pp. 2651-2656.
Gajewski et al., "Design, synthesis, and biological activity of novel triazole amino acids used to probe binding interactions between ligand and neutral amino acid transport protein SN1", Bioorganic & Medicinal Chemistry Letters, 17 (2007), pp. 4163-4166.
Jung et al., "The Stereochemistry of Addition of Trialkylammonium and Pyridinium Tetrafluoroborate Salts to Activated Acetylenes. Preparation of Novel Dienophiles for Diels-Alder Reactions", J. Am. Chem. Soc., 1988, 110(12), pp. 3965-3969.
Mindt et al., "Cu(I)-Catalyzed Intramolecular Cyclization of Alkynoic Acids in Aqueous Media: A "Click Side Reaction"", J. Org. Chem. 2007, 72, pp. 10247-10250.
Rostovtsev et al., "A Stepwise Huisgen Cycloaddition Process: Copper (I)-Catalyzed Regioselective "Ligatioin" of Azides and Terminal Alkynes", Angew. Chem. 2002, 114, Nr. 14, pp. 2708-2711.
Wang et al., "Synthesis and anticonvulsant activity of 1-substituted benzyl-N-substituted-1, 2, 3-triazole-4-formamides", Progress in Natual Science, vol. 16, No. 9, Sep. 2006, pp. 925-929.

* cited by examiner

*Primary Examiner* — Susannah Chung
(74) *Attorney, Agent, or Firm* — Rothwell, Figg, Ernst & Manbeck, P.C.

(57) ABSTRACT

The invention provides a novel process for the regioselective preparation of a compound of formula (I)

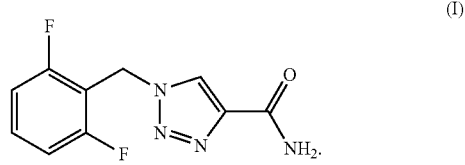

14 Claims, No Drawings

METHOD FOR THE PREPARATION OF RUFINAMIDE

The present invention relates to a novel process for the preparation of 1-(2,6-difluorobenzyl)-1H-1,2,3-triazole-4-carboxyamide.

TECHNOLOGICAL BACKGROUND 1-(2,6-Difluorobenzyl)-1H-1,2,3-triazole-4-carboxyamide, namely Rufinamide, of formula (I), is a known compound with anticonvulsive action, specifically used in combination with other antiepileptic medicaments for the treatment of Lennox-Gastaut syndrome, a rare form of epilepsy.

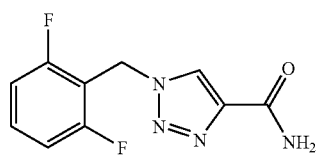

U.S. Pat. No. 4,789,680 discloses the synthesis of Rufinamide through 1-(2,6-difluorobenzyl)-1H-1,2,3-triazole-4-carboxylic acid of formula (II), which is in turn obtained by 1,3-dipolar cycloaddition of 2,6-difluorobenzyl azide of formula (III) with propiolic acid of formula (IV) (Scheme 1):

Scheme 1

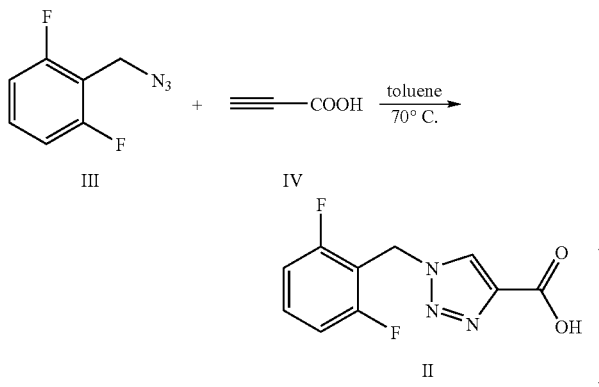

wherein the reaction is carried out at 70° C. reacting 2,6-difluorobenzyl azide with propiolic acid in toluene for several hours.

This procedure, however, suffers from various problems which limit its applicability on an industrial scale, in particular the following ones:

1) the thermal cycloaddition of the alkylazide of formula (III) with an alkyne of formula (IV), as defined above, leads to mixtures of 1,4 and 1,5 disubstituted regioisomer triazoles (Scheme 2).

Scheme 2

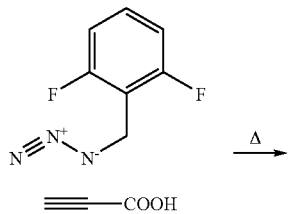

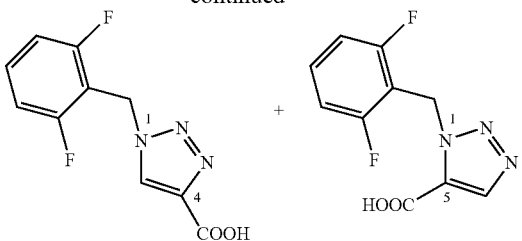

2) the alkyl azides are potentially explosive, the explosion risk increasing at higher temperatures, therefore it is safer to carry out reactions involving alkyl azides at about room temperature instead of high temperatures.

There is therefore the need for an alternative industrial process which allows to prepare Rufinamide on a large scale, safely and with improved regioisomeric selectivity and higher chemical purity.

DETAILED DISCLOSURE OF THE INVENTION

The object of the invention is a process for the preparation of Rufinamide, of formula (I),

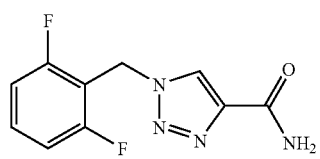

comprising the regioselective synthesis of a compound of formula (II),

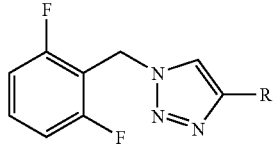

in which R is COOR$^1$ wherein R$^1$ is hydrogen, an alkali metal, a $C_1$-$C_8$ alkyl, aryl-$C_1$-$C_8$ alkyl, or aryl group; CN, CONH$_2$, COCH$_3$; or CH$_2$OR$^2$ wherein R$^2$ is hydrogen or a hydroxy-protecting group, by a process comprising the 1,3-dipolar cycloaddition reaction of 2,6-difluorobenzyl azide of formula (III)

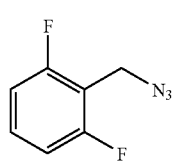

with a terminal alkyne of formula (IV),

wherein R is as defined above,
in the presence of a catalyst based on a monovalent copper salt;
to obtain a compound of formula (II) which is Rufinamide when in a compound of formula (IV) R is CONH$_2$; or a compound of formula (II) wherein R, being as defined above, is different from CONH$_2$, and its subsequent conversion to Rufinamide of formula (I).

$R^1$ as an alkali metal is typically sodium or potassium.

A $C_1$-$C_8$ alkyl group can be straight or branched, typically a $C_1$-$C_6$ alkyl group or residue, preferably a $C_1$-$C_4$ alkyl group, more preferably methyl, ethyl, propyl, isopropyl, butyl or tert-butyl.

An aryl group is for example phenyl or naphthyl.

An aryl-$C_1$-$C_8$ alkyl group, wherein the $C_1$-$C_8$ alkyl group is as defined above, is preferably benzyl or phenylethyl.

A hydroxy-protecting group is for example one of the protective groups commonly used in the sugar chemistry, in particular benzyl.

In a compound of formula (II) and (IV) R is preferably COOH or CONH$_2$.

A catalyst based on a monovalent copper salt is typically a compound of copper(I), having the following structure (V)

$$CuX \qquad (V)$$

wherein X is an organic or inorganic anion.

An inorganic anion can be for example a halide, typically a chloride or a iodide, a cyanide or un thiocyanate.

An organic anion can be acetate, thiophenolate, trifluoromethanesulfonate or hexafluorophosphate.

According to a preferred aspect of the invention, the catalyst based on a Cu(I) salt can be generated in situ by reaction between a copper(II) compound and a suitable reducing agent, wherein a copper(II) compound has typically one of the two following formulae (VI) or (VII)

$$CuY_2 \qquad (VI)$$

$$CuZ \qquad (VII)$$

in which Y is a monovalent anion, and Z is a bivalent anion.

A monovalent anion Y can be selected from e.g. a halide, such as chloride or bromide, nitrate, perchlorate, formate, acetate, trifluoroacetate, acetylacetonate, trifluoromethanesulfonate and tetrafluoroborate; preferably Y is a halide, in particular chloride.

A bivalent anion Z can be selected from e.g. sulfate, tartrate and carbonate, preferably Z is sulfate.

A suitable reducing agent is a compound, as known in the art, capable of reducing a bivalent copper salt to a monovalent copper salt and it can be selected, for example, from the group comprising sodium bisulfite or metabisulfite, reducing sugars, preferably glucose and fructose, ascorbic acid or its salts, e.g. sodium ascorbate. Preferably the copper(II) compound is CuSO$_4$ and the reducing agent is ascorbic acid.

The molar amount of copper (II) compound, for example CuSO$_4$, to the azide of formula (III) can be comprised between about 0.01% and 2%; preferably between about 0.1% and 1%.

The molar ratio of reducing agent to rameic ions is at least stoichiometric, preferably ranging from about 1 to 10.

The reaction between a compound of formula (III) and a compound of formula (IV), or a salt thereof, can be carried out in water or in an aqueous solution of a water-miscible polar organic solvent, or preferably in an anhydrous polar solvent.

Said polar solvent can be, for example, dimethylformamide, dimethylacetamide, a nitrile such as acetonitrile, dimethylsulfoxide; an alcohol, such as a $C_1$-$C_5$ alkanol, in particular methanol, ethanol, isopropanol or tert-butanol; a $C_3$-$C_7$ ketone, such as acetone, methyl-ethyl ketone; or mixtures of two or more than said solvents, preferably 2 or 3 thereof.

According to a preferred aspect of the invention, the reaction between a compound of formula (III) and a compound of formula (IV), or a salt thereof, can be carried out in an anhydrous polar organic solvent, selected from for example a polar organic solvent as reported above.

Preferably the reaction can be carried out in a $C_1$-$C_5$ alkanol, such as methanol, ethanol, isopropanol, or a mixture of two or more, preferably two or three $C_1$-$C_5$ alkanols, more preferably in methanol or ethanol.

It has surprisingly been found that the use of an anhydrous polar solvent, particularly an alkanol, instead of aqueous mixtures containing organic solvents, makes the reaction more controllable and reproducible from an industrial point of view, also as the reaction mixture is always homogeneous and monophase. This affects the reaction yields which are therefore more constant and reproducible. Furthermore, the reaction mixture work up and the final product recovery require fewer steps, thus affording the final product in short times, high yields and higher purity.

Typically, compounds of formula (III) and (IV) are reacted in the form of a solution thereof in the reaction solvent, as defined above, in a concentration between about 0.1 and 10 M, preferably between about 0.1 and 2M.

The reaction between a compound of formula (III) and a compound of formula (IV), or a salt thereof, can be carried out at a temperature ranging from about 0° C. to the reflux temperature of the reaction mixture, preferably between about 20 and 40° C.

A so obtained compound of formula (II) can be recovered from the reaction mixture, for example by crystallization.

A compound of formula (II) can be converted to another compound of formula (II) or to Rufinamide, according to known methods.

For example, a compound of formula (II) can be converted to another compound of formula (II) similarly to what reported above concerning the conversion of a compound of formula (IV) to another compound of formula (IV).

The subsequent conversion of a compound of formula (II) to Rufinamide of formula (I) can be carried out according to known techniques for the interconversion of functional groups. For example, the conversion of a compound of formula (II) wherein R is a carboxylic group to the respective amide can be effected according to the synthetic route reported in U.S. Pat. No. 4,789,680. The conversion of a compound of formula (II) wherein R is CN into Rufinamide of formula (I) can be carried out by basic hydrolysis.

The size of Rufinamide crystals, obtained according to the present process, is characterized by a $D_{50}$ value ranging from 25 to 250 m. If desired, said value can be reduced by micronisation or fine grinding.

A compound of formula (II), as well as Rufinamide, as obtainable by process of the invention, has chemical purity equal to or higher than 90% (HPLC), preferably equal to or higher than 99.9% (HPLC), which is a quality suitable to meet the regulatory requirements for medicinal products. In particular a compound of formula (II), or a salt thereof, as well as Rufinamide, have isomeric purity equal to or higher than 99.9%.

A compound of formula (III) is known and can be prepared starting from the corresponding commercially available 2,6-difluorobenzyl chloride or bromide, according to procedures well known to those skilled in the art.

Compounds of formula (IV) are known or can be prepared according to known methods. For example, compounds of formula (IV) wherein R is COOH, COCH$_3$, CH$_2$OH and COOCH$_3$ are commercially available. The compounds of formula (IV) wherein R is CONH$_2$ or CN can be prepared from a compound of formula (IV) wherein R is COOCH$_3$ according to the synthetic route reported in *J. Am. Chem. Soc.* 1988, 110(12), 3965-3969.

The following examples illustrate the invention.

EXAMPLE 1

Synthesis of Compound (III): 2,6-Difluorobenzyl azide

In a round-bottom flask NaN$_3$ (4.0 g, 61.5 mmoles) is dissolved in H$_2$O (20.5 ml), then 2,6-difluorobenzyl chloride (2.0 g, 12.3 mmoles) and tetrabutylammonium chloride (0.68 g, 2.46 mmoles) are added thereto. The reaction is kept at 40° C. for 1 h then cooled to room temperature and diluted with CH$_2$Cl$_2$. The phases are separated, the organic one is washed with water then dried over Na$_2$SO$_4$, filtered and concentrated under reduced pressure. Compound (III) is obtained as an oil in 88% yield.

$^1$H NMR (400 MHz, CDCl$_3$), ppm: 7.40-7.30 (m, 1H), 7.03-6.92 (m, 2H), 4.45 (s, 2H).

EXAMPLE 2

Synthesis of Compound (II): 1-(2,6-Difluorobenzyl)-1H-1,2,3-triazole-4-carboxylic acid 2,6-Difluorobenzyl azide (III) (3.5 g, 20.7 mmoles) is suspended in a H$_2$O-tBuOH 1:1 mixture (80 ml), then propiolic acid (1.59 g, 22.8 mmoles), an ascorbic acid 1M solution (2.1 ml) and a CuSO$_4$ 0.3 M solution (0.7 ml) are added thereto. The reaction mixture is kept at 40° C., under stirring and is completed after 2 h. The mixture is left to cool at room temperature thereby precipitating the product. The solid is filtered off on a Buchner filter, washed with ethyl ether and dried under vacuum.

A crystalline white solid is obtained in 71% yield. Mother liquors are concentrated under reduced pressure and the residue is subjected to further crystallization. Overall yield: 94%.

$^1$H NMR (400 MHz, DMSO-d$_6$), δ ppm: 8.74 (s, 1H), 7.58-7.47 (m, 1H), 7.19 (m, 2H), 5.73 (s, 2H).

EXAMPLE 3

Synthesis of Compound (II): 1-(2,6-Difluorobenzyl)-1H-1,2,3-triazole-4-carboxylic acid 2,6-Difluorobenzyl azide (III) (7.0 g, 41.4 mmoles) is suspended in a H$_2$O-tBuOH 1:1 mixture (120 ml), then propiolic acid (3.19 g, 45.6 mmoles), an ascorbic acid 1M solution (4.2 ml) and a CuSO$_4$ 0.3 M solution (1.4 ml) are added thereto. The reaction mixture is kept at 25° C. under stirring and is completed after 2 h. The mixture is left to cool at room temperature thereby precipitating the product. The solid is filtered off on a Buchner filter, washed with ethyl ether and dried under vacuum.

A crystalline white solid is obtained in 80% yield.

$^1$H NMR (400 MHz, DMSO-d$_6$), δ ppm: 8.74 (s, 1H), 7.58-7.47 (m, 1H), 7.19 (m, 2H), 5.73 (s, 2H).

EXAMPLE 4

Synthesis of Compound (I): 1-(2,6-Difluorobenzyl)-1H-1,2,3-triazole-4-carboxyamide (Rufinamide)

The carboxylic acid (II) (1.5 g, 6.27 mmoles) is treated at room temperature under stirring with thionyl chloride (15 ml). After completion of the addition, the reaction mixture is refluxed for 1 h. The thionyl chloride excess and the other reaction volatiles distilled off first at atmospheric pressure then under reduced pressure. The resulting acid chloride is solid at room temperature, and is dissolved in toluene (15 ml). The solution is placed in a separatory funnel, then slowly added to an ammonia concentrated aqueous solution (15 ml, 30% by weight), cooled in iced water bath. After completion of the addition, the mixture is left to reach room temperature and diluted with ethanol. The abundant precipitate formed is filtered off on a Buchner filter. Yield 91%.

$^1$H NMR (400 MHz, DMSO-d$_6$), δ ppm: 8.56 (s, 1H), 7.87 (bs, 1H), 7.60-7.43 (m, 2H), 7.20 (m, 2H), 5.72 (s, 2H).

EXAMPLE 5

Synthesis of Compound (IV): Propiolamide

Methyl propiolate (IV) (72 g, 0.86 mol) is slowly dropped into a 33% ammonia aqueous solution (240 ml) cooled at −30° C. The reaction mixture is kept under stirring at the same temperature for 1 hour, then slowly brought again to about 25° C. The reaction is concentrated under reduced pressure to a residue, which is then taken up with methyl tert-butyl ether (350 ml) and the solution is dried over Na$_2$SO$_4$, then filtered and concentrated under reduced pressure to obtain 53 g of a yellow solid which is not purified but directly used in the subsequent reaction. Yield: 89%.

EXAMPLE 6

Synthesis of Compound (I): 1-(2,6-Difluorobenzyl)-1H-1,2,3-triazole-4-carboxyamide (Rufinamide)

A 500 ml round-bottom flask is loaded with 2,6-difluorobenzyl azide (100 g, 0.59 mole) dissolved in methanol (300 ml), then propiolamide (49 g, 0.71 mole) obtained according to Example 5 is added under stirring to obtain a solution. Afterwards, CuSO$_4$ pentahydrate (1.46 g, 5.9 mmoles) and ascorbic acid (5.19 g, 29.6 mmoles) are added in succession. The reaction mixture spontaneously reaches 40° C. and is kept under stirring for 4 hours at the same temperature. The formed solid is then filtered off, washed with methanol and water, and dried in an oven at 50° C., thereby affording 133 g of a solid crude in 89% yield. The solid is suspended in water (300 ml), the suspension is treated with 33% aqueous ammonia (50 ml) and left under stirring for 3 hours, then the resulting white solid is filtered and dried in an oven. 130 g of a crystalline solid are obtained in 87% yield.

$^1$H NMR (400 MHz, DMSO-d$_6$), δ ppm: 8.56 (s, 1H), 7.87 (bs, 1H), 7.60-7.43 (m, 2H), 7.20 (m, 2H), 5.72 (s, 2H).

EXAMPLE 7

Synthesis of Compound (II): Methyl 1-(2,6-difluorobenzyl)-1H-1,2,3-triazole-4-carboxylate 2,6-Difluorobenzyl azide (3.0 g, 17.7 mmoles) is suspended in ethanol (30 ml), then methyl propiolate (IV) (1.6 g, 19.6 mmoles), ascorbic acid (317 mg, 1.8 mmoles) and CuSO$_4$ pentahydrate (50 mg, 0.18 mmole) are added. The reaction mixture is kept at 25° C. under stirring overnight. The mixture is concentrated, taken up with ethyl acetate and washed with an ammonia diluted solution. The organic phase is dried, filtered, concentrated under reduced pressure. A crystalline white solid is obtained in 94% yield.

$^1$H NMR (400 MHz, DMSO-d$_6$), δ ppm: 8.86 (s, 1H), 7.52 (m, 1H), 7.27-7.12 (m, 2H), 5.74 (s, 2H), 3.83 (s, 3H).

EXAMPLE 8

Synthesis of Compound (I): 1-(2,6-Difluorobenzyl)-1H-1,2,3-triazole-4-carboxyamide (Rufinamide)

Methyl 1-(2,6-difluorobenzyl)-1H-1,2,3-triazole-4-carboxylate (II) (10.6 g, 41.9 mmoles), prepared as reported in Example 7, is dissolved in methanol (10 ml) and treated at room temperature under stirring with a 30% ammonia aqueous solution (40 ml), then the reaction mixture is refluxed and kept under stirring for 3 hours. The mixture is cooled to 20° C., then diluted with water, filtered, and the resulting white solid is washed with water and dried in a static dryer at 50° C. Rufinamide (8.7 g) is obtained as a crystalline white solid in 87% yield.

$^1$H NMR (400 MHz, DMSO-d$_6$), δ ppm: 8.56 (s, 1H), 7.87 (bs, 1H), 7.60-7.43 (m, 2H), 7.20 (m, 2H), 5.72 (s, 2H).

The invention claimed is:

1. A process for the preparation of Rufinamide, of formula (I),

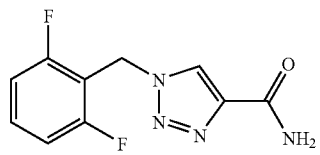
(I)

comprising the regioselective preparation of a compound of formula (II),

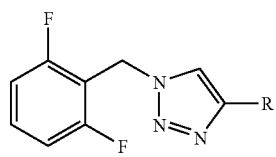
(II)

in which R is COOR$^1$ wherein R$^1$ is hydrogen, an alkali metal, a C$_1$-C$_8$ alkyl, aryl-C$_1$-C$_8$ alkyl, or aryl group; CN, CONH$_2$, COCH$_3$ or CH$_2$OR$^2$ wherein R$^2$ is hydrogen or a hydroxy-protecting group, by a process comprising the 1,3-dipolar cycloaddition reaction of 2,6-difluorobenzyl azide of formula (III)

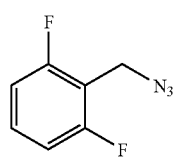
(III)

with a terminal alkyne of formula (IV),

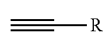
(IV)

wherein R is as defined above,
in the presence of a catalyst based on a monovalent copper salt;

to obtain a compound of formula (II) which is Rufinamide when in a compound of formula (IV) R is CONH$_2$; or a compound of formula (II) wherein R, being as defined above, is different from CONH$_2$, and its subsequent conversion to Rufinamide of formula (I).

2. The process according to claim 1, wherein a catalyst based on a monovalent copper salt is a copper(I) compound of the following formula (V)

CuX      (V)

wherein X is an organic or inorganic anion.

3. The process according to claim 1, wherein the catalyst based on a monovalent copper salt is generated in situ by reaction of a copper(II) compound with a reducing agent, wherein the copper(II) compound has one of the two following formulae (VI) or (VII)

CuY$_2$      (VI)

CuZ      (VII)

in which Y is a monovalent anion, and Z is a bivalent anion.

4. The process according to claim 3, wherein the monovalent anion Y is selected from a halide, nitrate, perchlorate, formate, acetate, trifluoroacetate, acetylacetonate, trifluoromethanesulfonate and tetrafluoroborate; and the bivalent anion Z is selected from sulfate, tartrate and carbonate.

5. The process according to claim 3, wherein the reducing agent is selected from the group comprising sodium bisulfite and metabisulfite, a reducing sugar, ascorbic acid or a salt thereof.

6. The process according to claim 3, wherein the copper(II) compound is CuSO$_4$ and the reducing agent is ascorbic acid.

7. The process according to claim 3, wherein the molar ratio of copper(II) compound to azide of formula (III) is comprised between about 0.01% and 2%.

8. The process according to claim 1 in which the molar amount of reducing agent to rameic ions is at least stoichiometric.

9. The process according to claim 1, wherein the reaction between a compound of formula (III) and a compound of formula (IV), or a salt thereof, is carried out in water or in an aqueous solution of a water-miscible polar organic solvent, or in an anhydrous polar organic solvent.

10. The process according to claim 9 wherein the reaction between a compound of formula (III) and a compound of formula (IV), or a salt thereof, is carried out in an anhydrous polar organic solvent.

11. The process according to claim 9 wherein the polar organic solvent is selected from dimethylformamide, dimethylacetamide, a nitrile, dimethylsulfoxide; a C$_1$-C$_5$ alkanol; a C$_3$-C$_7$ ketone; or a mixture of two or more of said solvents.

12. The process according to claim 10 wherein the polar organic solvent is a C$_1$-C$_5$ alkanol, or a mixture of two or more C$_1$-C$_5$ alkanols.

13. The process according to claim 12 wherein the polar organic solvent is methanol or ethanol.

14. The process according to claim 9, wherein the compounds of formula (III) and (IV) are reacted in the form of a solution thereof in the reaction solvent, in a concentration between about 0.1 and 10M.

* * * * *